United States Patent
Siegel et al.

(10) Patent No.: US 9,466,024 B2
(45) Date of Patent: Oct. 11, 2016

(54) LEARNING HEALTH SYSTEMS AND METHODS

(71) Applicants: Neil G. Siegel, Rolling Hills Estates, CA (US); Sam S. Shekar, Potomac, MD (US); Jeffrey C. Yu, Castro Valley, CA (US); Robert Michael Lefler, Stephens City, VA (US)

(72) Inventors: Neil G. Siegel, Rolling Hills Estates, CA (US); Sam S. Shekar, Potomac, MD (US); Jeffrey C. Yu, Castro Valley, CA (US); Robert Michael Lefler, Stephens City, VA (US)

(73) Assignee: Northrop Grumman Systems Corporation, Falls Church, VA (US)

( * ) Notice: Subject to any disclaimer, the term of this patent is extended or adjusted under 35 U.S.C. 154(b) by 609 days.

(21) Appl. No.: 13/837,370

(22) Filed: Mar. 15, 2013

(65) Prior Publication Data

US 2014/0279721 A1 Sep. 18, 2014

(51) Int. Cl.
*G06N 5/00* (2006.01)
*G06F 1/00* (2006.01)
*G06N 5/02* (2006.01)
*G06N 99/00* (2010.01)
*G06F 19/28* (2011.01)

(52) U.S. Cl.
CPC ............. *G06N 5/02* (2013.01); *G06F 19/28* (2013.01); *G06N 99/005* (2013.01)

(58) Field of Classification Search
CPC ........... G06N 5/02; G06N 5/04; G06N 5/048
See application file for complete search history.

(56) References Cited

U.S. PATENT DOCUMENTS

2014/0045714 A1* 2/2014 Gerszten et al. ............. 506/9
2014/0170735 A1* 6/2014 Holmes ..................... 435/287.1

OTHER PUBLICATIONS

International Search Report for corresponding PCT/US2014/019022, completed Jun. 18, 2014 by Constanze Schmitt.
J. Herrero: "GEPAS": a web-based resource for microarray gene expression data analysis, Nucleic Acids Research, vol. 31, No. 13, Jul. 1, 2003, pp. 3461-3467, XP055123687, DOI: 10.1093/nar/gkg591 abstract p. 3462, col. 2, paragraph 4—p. 3463, col. 2, paragraph 2; figs. 1,3.
Ziv Bar-Joseph et al: "Studying and modeling dynamic biological processes using time-series gene expression data", Nature Reviews Genetics, vol. 13, No. 8, Jul. 18, 2012, pp. 552-564, XP055123855, ISSN: 1471-0056, DOI: 10.1038/nrg3244 abstract p. 557, col. 1, paragraph 1-paragraph 3; figs. 1, 3; table 1.

(Continued)

*Primary Examiner* — Stanley K Hill
*Assistant Examiner* — Kalpana Bharadwaj
(74) *Attorney, Agent, or Firm* — Tarolli, Sundheim, Covell & Tummino LLP

(57) ABSTRACT

A learning health system and associated methods are provided. Biochemical assays are conducted at scheduled intervals on blood samples taken from an individual to provide, for each of a plurality of biochemical parameters, a time series of values representing the individual. Clinical parameters associated with the individual are extracted from a knowledge base. Genomic parameters are determined for the individual. An expected time series is calculated for each of a plural subset of the plurality of biochemical parameters from at least the clinical parameters and the genomic parameters. For each of the plural subset of biochemical parameters, the time series of values representing the individual is compared to the calculated expected time series to determine a likelihood of each of a plurality of conditions for the individual. The likelihood of at least one of the plurality of conditions is communicated to a user.

17 Claims, 3 Drawing Sheets

(56) References Cited

OTHER PUBLICATIONS

Edwin P. Romijn et al: "Expression clustering reveals detailed co-expression patterns of functionally related proteins during B cell differentiation: a proteomic study using a combination of One-dimensional gel electrophoresis, LC-MS/MS, and stable isotope labeling by amino acids in cell culture (SILAC)", Molecular & cellular proteomics: MCP, Sep. 1, 2005, pp. 1297-1310, XP055123812, DOI: 10.1074/mcp.M500123-MCP200 Retrieved from the Internet: URL:http://www.ncbi.nlm.nih.gov/pubmed/15961381 [retrieved on Jun. 17, 2014] abstract.

I.G. Costa et al: "Constrained mixture estimation for analysis and robust classification of clinical time series", Bioinformatics, vol. 25, No. 12, May 28, 2009, pp. i16-i14, XP055123849, ISSN: 1367-4803, DOI: 10.1093/bioinformatics/btp222 abstract p. i6, col. 1, paragraph 3—p. i8,col. 1, paragraph 4; figs.1, 6.

* cited by examiner

LEARNING HEALTH SYSTEMS AND METHODS

TECHNICAL FIELD

This invention relates to healthcare information management, and more particularly, to learning health systems and methods.

BACKGROUND

The healthcare industry provides goods and services to treat patients with curative, preventive, rehabilitative, and palliative care. The modern healthcare sector is divided into many sub-sectors, and depends on interdisciplinary teams of trained professionals and paraprofessionals to meet health needs of individuals and populations. The healthcare industry is one of the world's largest and fastest-growing industries. Consuming over ten percent of gross domestic product (GDP) of most developed nations, healthcare can form an enormous part of a country's economy. Currently, the United States spends over seventeen percent of GDP on healthcare, and this amount is expected to grow at a nearly six percent annual rate. Many attempts have been made to slow down, and eventually reverse, this increase in healthcare spending, however, most attempts have failed or have not had an impact as yet. Contributing to the cost impacts, healthcare is often provided at later stages of illness—based on current technologies and applications—rather than on earlier stages of illness, where care would be less intensive and costs would be much lower.

SUMMARY

In accordance with an aspect of the present invention, a method is provided for personalized healthcare support. Biochemical assays are conducted at scheduled intervals on blood samples taken from an individual to provide, for each of a plurality of biochemical parameters, a time series of values representing the individual. A plurality of clinical parameters associated with the individual are extracted from a knowledge base. A plurality of genomic parameters are determined for the individual. An expected time series is calculated for each of a plural subset of the plurality of biochemical parameters from at least the clinical parameters and the genomic parameters. For each of the plural subset of biochemical parameters, the time series of values representing the individual is compared to the calculated expected time series to determine a likelihood of each of a plurality of conditions for the individual. The likelihood of at least one of the plurality of conditions is communicated to a user.

In accordance with another aspect of the present invention, a learning health system includes a knowledge base storing a record for each of a population of patients. A given record includes a time series of values of a plurality of biochemical parameters taken from biochemical assays performed at scheduled intervals, a plurality of genetic markers, and a plurality of clinical parameters associated with the patient. The population of patients includes, for each of a plurality of conditions of interest, a set of patients having the condition and a set of patients not having the condition. A baseline calculation component is configured to calculate, for a given patient, an expected time series for each of a plural subset of the biochemical parameters from at least the clinical parameters and the genomic parameters associated with the patient. An analytics and modeling component is configured to determine a deviation of the time series of values from the calculated expected time series and apply the deviation as an input to a predictive model associated with one of the plurality of conditions. The predictive model is derived from data associated with each of the set of patients having the condition and the set of patients not having the condition and configured to determine the likelihood of that the patient has the condition from at least one parameter derived from the determined deviation. A user interface is configured to provide the determined likelihood that the patient has the condition to a user.

In accordance with still another aspect of the present invention, a method is provided for personalized healthcare. Biochemical assays are conducted at scheduled intervals on blood samples taken from a patient to provide, for each of a plurality of biochemical parameters, a time series of values representing the patient. A plurality of clinical parameters associated with the patient are extracted from a knowledge base. A plurality of genomic parameters are determined for the patient. A plurality of cohort parameters are extracted from respective series of biochemical assays representing individuals who are associated with the patient. An expected time series is calculated for each of a plural subset of the plurality of biochemical parameters from at least the clinical parameters, the cohort parameters, and the genomic parameters. A deviation of the time series of values from the calculated expected time series is determined. The deviation is applied as an input to a predictive model associated with a condition. The predictive model is configured to determine the likelihood of the condition from at least one parameter derived from the determined deviation. The user is provided with a with a healthcare treatment course of action based on the likelihood of the conditions.

DETAILED DESCRIPTION

Figure 1:
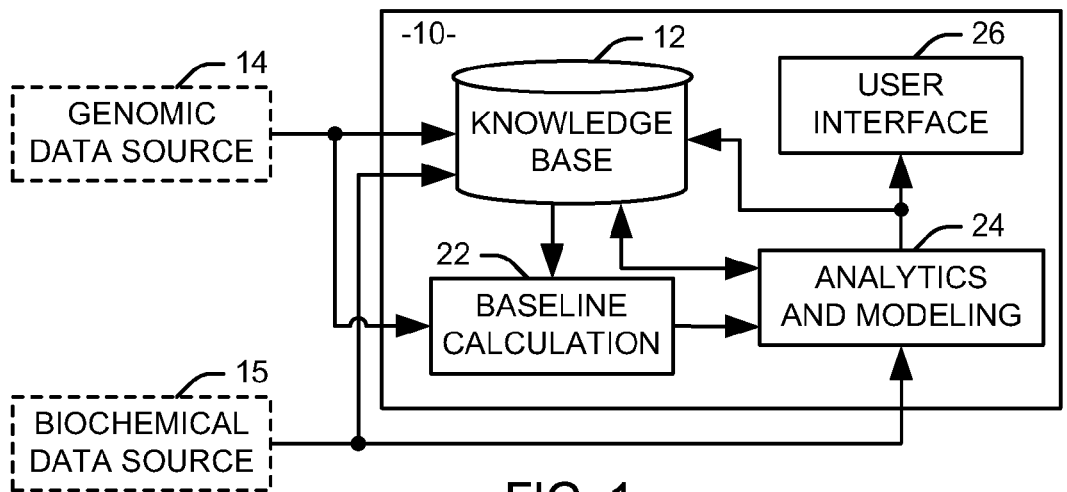
FIG. 1 illustrates a learning healthcare system in accordance with an aspect of the present invention.

Healthcare in the many nations is driven by medical protocols, which are guidelines for when and how to perform diagnostic and clinical activities on an individual. These protocols, however, are created with, at best, superficial reference to any significant knowledge of the individual. The inventors have found that genomics can be helpful in customizing care, but that it will be necessary to supplement genomics data with other data that provide more insight into ones health condition at the time of the measurement. Genomics is largely about risk of a condition, while other measurements are about present health status.

Accordingly, the inventors have determined that data about an individual—derived from proteomics and other sources—can allow for a new type of medical protocol. This protocol adapts to deep medical knowledge of an individual, both their current medical and proteomic state and their own trend and history over time, as a replacement for today's medical protocols that are rigid and rely on generalizations based on populations, rather than the medical state of an individual. The practice of medicine in accordance with such new, individualized medical protocols is expected to provide significant cost savings while simultaneously improving average individual health.

In one implementation, a low-cost, minimally intrusive, proteomic-based test can be periodically given to each of a population of patients, for example, on respective schedules informed by individual genomics, can be used for a new approach to personalized healthcare. Results from this periodic test are used to create individualized longitudinal medical data, vastly improving the efficacy of any later diagnosis. The results can also be used provide individualized medical data that can be used to provide a personalized medical protocol using deep medical knowledge of an individual and his/her own trend and history over time, and provide early indications of onset of specific conditions that may require treatment or life-style modification. In essence, the proteomic-based test acts as the "gatekeeper" to personalized care. This approach shifts the current medical model from a reactive, symptom-based approach to a predictive/preventive approach based on personalized information.

In one implementation, the system can receive data from a simultaneous assay of thousands of proteins from a single drop of blood. Combining these data with the data in electronic healthcare records and other sources can provide both current and longitudinal information about each individualized patient. Using a data base of current medical knowledge and best practices, in combination with a set of "causality cases", which relate the sensed medical signals to current and predicted conditions and diagnoses, can provide rapid, accurate, and personalized diagnoses and recommendations for a healthcare treatment course of action for thousands of conditions simultaneously, all from a single blood test. This approach improves outcomes by basing diagnosis and recommendations on far more data than are available today from any affordable diagnostic procedure, and decreases costs by substituting an inexpensive test for a series of expensive ones, enabling earlier detection and intervention, mechanizing the sharing of test results across specialists and institutions, reducing the variation in clinical decision practices, and significantly reducing the broad range of individuals who are currently and unnecessarily screened, tested, and treated. Further, by maintaining all of this data in a centralized knowledge base, research into new causality cases can be substantially facilitated.

Healthcare also is subject to huge variation in practice. It is not enough to have personalized data that indicate a patient's condition. The recommended course-of-action must reflect appropriate practices consistently and incorporate evidence-based standards. Data indicate, however, that unjustified variation in medication practice accounts for between thirty to fifty percent of the total U.S. healthcare spending, in addition to causing harm and even death. Improving quality starts with reducing variation, rather than simply improving the population mean, and this is addressed by a learning health system in accordance with an aspect of the present invention. At the scale of a national healthcare system, reducing variation first entails creating evidence for best practices based upon new findings, and incorporating that evidence into recommendations for patients and healthcare providers.

The proposed system provides a number of advantages over the traditional healthcare approach. For example, the system allows consumers to know, based on objective data, when they need to enter the healthcare system to seek detailed diagnosis and treatment. At present, people make this determination with only a minimum of information, much of which is subjective or unreliable (e.g., how they "feel," "what hurts," temperature, etc.). The system also permits the healthcare practitioner at the patient's point-of-entry to rapidly evaluate changes and off-nominal conditions in the patient across a wide range of conditions and factors, based on minimally invasive technologies and data sources with a high degree of certainty, and route the patient to appropriate tests, screening, specialist practitioners, and procedures, thereby saving time, money, and frustration. Variation in healthcare practice can be materially reduced by conjoining detailed diagnostic information with evidence of clinical effectiveness applied to specific patient strata, allowing healthcare systems to improve and target delivery of care. The efficiency of the healthcare system is also increased by more proactively identifying and monitoring sick people earlier in their disease course, so that they come into treatment more effectively and with reduced use of more intensive treatments. Finally, practitioners can become more efficient and effective in their practice through periodic incorporation of new "causality cases," that is, the latest information about measurable health indicators that indicate and predict health factors, diseases, and tendencies, into a computer database, which can then be linked automatically to personalized healthcare options.

FIG. 1 illustrates a learning health system 10 in accordance with an aspect of the present invention. It will be appreciated that the system can be implemented as machine executable instructions stored on a set of at least one non-transitory computer readable medium and executed by an associated processor, dedicated hardware, or a combination of dedicated hardware and software components. The system 10 includes a knowledge base 12 storing a record for each of a population of patients. The knowledge base 12 can include data received from each of a genomic data source 14, representing a genetic mapping of an individual to locate genetic markers, and a biochemical data source 15, representing the levels of various biochemical parameters for the individual as derived from biochemical assays. In accordance with an aspect of the present invention, the biochemical assays can be scheduled at regular intervals, such that even healthy patients are encouraged to provide a usable time series of biochemical parameters.

Accordingly, each record can include a time series of values for each a plurality of biochemical parameters taken from biochemical assays performed at scheduled intervals, a plurality of genetic markers, and a plurality of clinical parameters associated with the patient. The plurality of clinical parameters can be extracted, for example from electronic health record databases and include previous diagnoses and procedures, clinical observations, longitudinal biometric parameters (e.g., age, weight, blood pressure, temperature, glucose levels, etc.), and a family medical history. It will be appreciated that the population of patients can include, for each of a plurality of conditions of interest, a set of patients having the condition and a set of patients not having the condition. In addition to patient records, the knowledge base 12 can also contain statistics representing incident rates and measured outcomes for various disorders as well as data on causal links between available parameters and conditions drawn from medical research. In one implementation, a research interface (not shown) can be provided for extracting data from available medical research, including an information extraction component to reduce an unstructured source of research, such as a journal article, into a template compatible with the knowledge base.

A baseline calculation component 22 is configured to calculate, for a given patient, an expected time series for a patient's biochemical parameters from at least the clinical parameters and the genomic parameters associated with the patient. While the system 10, evaluates patients for a large number of conditions in parallel based on the biochemical assays, it will be appreciated that not every biochemical parameter is relevant to every situation and patient. Accordingly, the baseline calculation component 22 may selectively calculate an expected time series for each of a plural subset of the available biochemical parameters to preserve processing resources.

An analytics and modeling component 24 is configured to determine a deviation of the time series of values from the calculated expected time series and apply the deviation as an input to one or more predictive models associated with respective conditions of the plurality of conditions. Each predictive model can be derived from data in the knowledge base 12 associated with each of the set of patients having the condition and the set of patients not having the condition. For example, the predictive models can include appropriate supervised learning algorithms, such as regression models, artificial neural networks, support vector machines, and statistical classifiers, trained on data from the knowledge base. Each predictive model predicts a likelihood of one of a plurality of disorders according to deviations between the measured biometric parameters and the baseline from the deviation. For example, the predictive model can operate on one or more of a distance metric (e.g., Euclidian, Mahalanobis, Manhattan), difference between the measured and expected time series can be used as a predictive feature. Alternatively, the difference in the time series across a number of most recent data points can be used as features. In general, it will be appreciated that a number of descriptive statistics representing differences between two time series can be calculated, and any of these measures may be useful as a predictive feature. It will be appreciated that a given model can include parameters beside the calculated deviation as well, and that these additional parameters can be drawn from the knowledge base. In one implementation, the results of the predictive modeling can be supplemented with an actual course of treatment and a measured clinical outcome and fed back to the knowledge base 12 for use in generating addition causality cases.

In one implementation, the analytics and modeling component 24 can include a data mining component (not shown) configured to perform a plurality of unsupervised learning algorithms on the knowledge base 12 to determine at least one causality case relating one of the clinical parameters and the genomic parameters to the condition. The determined causality case can, once confirmed by subject matter experts, be used to refine existing predictive models or generate new predictive models. To facilities review of the newly generated causality cases, the analytics and modeling component can also include an analytics component (not shown) available to the user through a user interface 26 and configured to retrieve data from the knowledge base 12 and an associated database (not shown). Under the guidance of a subject matter expert, the analytics component can run various queries on the knowledge base and the data base to provide evidence supporting or refuting a given causality case. In one implementation, the analytics and modeling component also includes a rules engine (not shown) that evaluates causality cases determined by the data mining component, according to an associated set of rules, to determine which variables, associated with the causality cases, present a highest likelihood of providing actionable results if evaluated with the analytics component. By limiting the analysis to parameters believed to be relevant, this rules engine can be used to conserve processing resources and decrease the likelihood of false positives in determining interrelationships among the data stored in the knowledge base 12.

The user interface 26 is configured to provide the determined likelihood that the patient has the condition to a user. The user interface 26 can include visualization tools to allow the user to see a graphical comparison of the expected time series of biochemical parameter values and an actual time series of biochemical parameter values. In one implementation, the user interface includes a patient dashboard (not shown) configured to communicate each of the determined likelihood of the condition, a healthcare treatment course of action, and a scheduled next biochemical assay. Accordingly, the patient can be instructed to enter the healthcare system at an appropriate time based on the biochemical analysis. The patient dashboard may also include links to information about any diagnosed disorders and recommended treatment option.

The user interface 26 can also include a clinician decision support component (not shown) configured to communicate a recommended protocol of care to a clinician based on the determined likelihood that a patient has a condition. By making the data from the knowledge base 12 and predictive models available to all stakeholders in the healthcare system, the user interface 26 can ensure transparency of the recommended courses of actions to clinicians and patients and ensure that researchers have easy access to data stored in the knowledge base to allow for the generation of new causality cases and predictive models.

Figure 2:
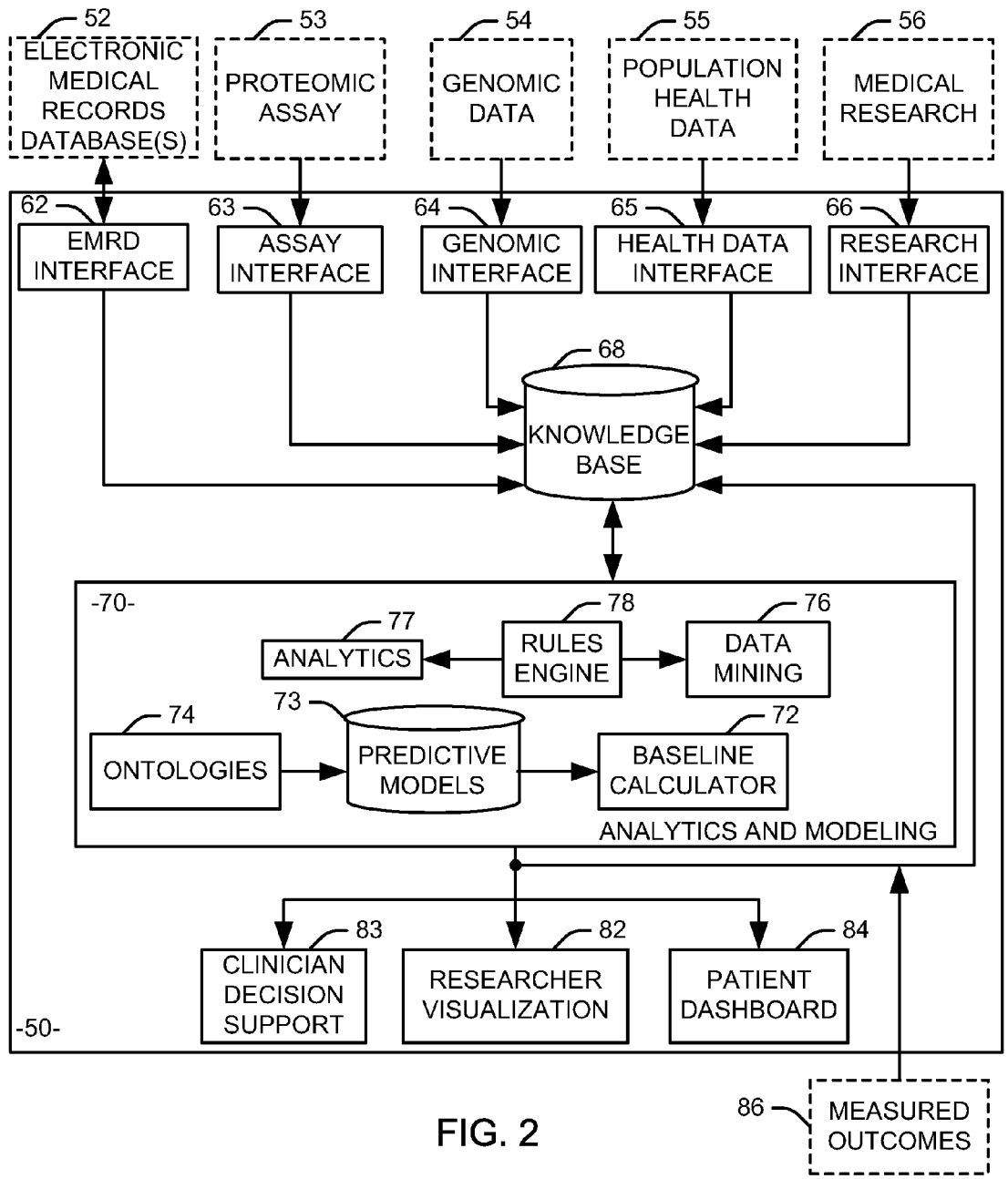
FIG. 2 illustrates one implementation of a learning healthcare information processing system in accordance with an aspect of the present invention.

FIG. 2 illustrates one implementation of a learning healthcare information processing system 50 in accordance with an aspect of the present invention. In the illustrated implementation, the system 50 receives data from a plurality of data sources 52-56 external to the system, indicated in a dashed outline, through respective data interfaces 62-65 and processes that data to provide recommendations to patients, clinicians, and researches based on accumulated data from these resources. A first data source 52 includes electronic medical record databases, with each electronic medical record database containing medical data for a plurality of patients comprising, for example, previous diagnoses and procedures, clinical observations, longitudinal biometric parameters, and a family medical history. Examples of electronic medical record databases that could be compatible with the information processing system can include the Armed Forces Health Longitudinal Technology Application (AHLTA), the Veterans Health Information Systems and Technology Architecture (VISTA), and similar such databases maintained by large healthcare organizations with a significant patient base. Records from these databases can be provided through an electronic medical record database (EMRD) interface 62 to convert the retrieved records to an appropriate format for a knowledge base 68 associated with the healthcare information processing system 50. In one implementation, the full record stored in the electronic medical record database is truncated by the interface to a set of clinically relevant observations.

The data sources can also include a biometric assay 53 taken from a large population of patients. In the illustrated implementation, a proteomic assay is utilized, but it will be appreciated that other biometric assays can also utilized, including pharmacogenomic assays, metabolomic assays, epigenomic assays, as well as interactomic, transcriptomic, and microbiomic data. In one implementation, the proteomic assay 53 can detect around ten thousand proteins and be administered at scheduled intervals to provide a time series of blood levels for each of the ten thousand proteins. An assay interface 63 can format the assay data for the knowledge base 68 and associate identifying information of the assays with corresponding patient records in the knowledge base. The assay interface 63 can also normalize the proteomic data to a scale utilized by the knowledge base 68. In one implementation, the proteomic assay can be reduced to a vector of clinically important features to be provided to the knowledge base 68, with the full assay compressed and stored in a separate mass storage with time-stamped line from the patient file to the full assay.

The system 50 can also utilize genomic data 54 from a population of patients. For example, the genomics data can be captured for each patient via an appropriate assay and provided to the system through a genomics interface 64. The genomics interface 64 extracts known genetic markers from the genome, formats the extracted data for the knowledge base 68 and associates identifying information of the genetic information with corresponding patient records in the knowledge base, for example, via a link from the patient record to the extracted markers.

Information and statistics from population health data sources 55 can be provided through a health data interface 65. Population health data sources 55 include, for example, structured or semi-structured data representing incident rates and measured outcomes for various disorders. Examples of population health data sources 55 can include the Surveillance, Epidemiology, and End Results (SEER) program maintained by the National Cancer Institute, the Behavioral Risk Factor Surveillance System (BRFSS) maintained by the Centers for Disease Control and Prevention, the Healthcare Cost and Utilization Project (HCUP) maintained by the Agency for Healthcare Research and Quality, and the Food and Drug Administration Adverse Event Reporting System (FAERS). The health data interface 65 can convert the structured and semi-structured data maintained in these resources into an appropriate format for a knowledge base 68 associated with the system 50.

Finally, data concerning causality factors for various disorders can be captured from medical research literature 56 and provided to the knowledge base 68 through a research interface 66. Exemplary sources of medical research literature can include the Medline collection from the National Library of Medicine, the PubMed collection, the GenBank sequence database, and the Gene Expression Omnibus repository maintained by the National Center for Biotechnology, the ArrayExpress and InterPro databases maintained by the European Bioinformatics Institute, the ImmPort immunology database and the Database for Annotation, Visualization, and Integrated Discovery maintained by the National Institute of Allergy and Infectious Diseases, and the UniProt knowledge bases, as well as Internet publications, such as Wikipedia, WebMD, health organization websites, and similar information sources. Since the medical research data 56 can include unstructured data, the research interface 66 can include an information extraction component to reduce an unstructured source of research, such as a journal article, into a format compatible with the knowledge base 68. The information extraction component breaks down the unstructured source into individual words or phrases, interprets the context and meaning of the various words or phrases, and uses the extracted information to generate a template representing the unstructured source. In one implementation, the generated template can be reviewed by a human expert in a field relevant to the unstructured source to ensure that the information provided to the knowledge base 68 is accurate.

The knowledge base 68 can be implemented as a massively parallel system to provide a low response time and significant scalability for increasing amounts of data. In one implementation, the knowledge base 68 can include a plurality of geographically remote regional caches, such that data associated with a given patient population is easily and quickly accessible to local clinicians. Each cache is operatively connected to a master knowledge base to allow for analysis of the data in aggregate for researchers, and can be fed data by the master knowledge base according to scheduled appointments. Requests from emergency rooms and other unscheduled sources of care can be prioritized to allow real-time or near real-time access to patient information. Information in the caches can be replaced such that data that has been least recently used is replaced. The knowledge base 68 stores at least clinical observations, proteomics, and genomics from various patients, including data for both a healthy population and a population of individuals that have disease syndromes, allergic reactions, or some other undesirable clinical outcome. The knowledge base 68 include will be a mixture of active data in the knowledge base, for example, triggers supported by a notification subsystem, and a rule base using a scalable rules engine.

In accordance with an aspect of the present invention, an analytics and modeling component 70 can interact with the knowledge base 68 to determine relationships among the data. The function of the analytics and data modeling component 70 can be roughly divided into what is referred to herein as "forward analytics," in which the likelihood of any of a variety of conditions for a given patient can be predicted by comparing data associated with the patient to data from the larger population, and "backwards analytics," in which data from a large population of patients is mined to determine relationships between clinical parameters and identified conditions.

In one example of a forward analytics process, a baseline calculator 72 can be configured to calculate, for a given patient, an expected longitudinal progression of a biometric parameter, such as the levels of clinically relevant proteins from the proteomic assays 53. In general, the baseline is determined according to an amalgamation of biometric parameters recorded for cohorts of similarly situated patients, that is, patients who either live or work in the same location as the patient, have similar genetic markers, have similar medical histories, or otherwise have clinically relevant parameters in common with the patient. The baseline can be calculated, for example, via one or more statistical models that utilize this data to determine what an appropriate level or range of levels for each of a plurality of clinical relevant biometric parameters would be for the patient given his or her medical history, including not only diagnoses and conditions, but also longitudinally recorded parameters such as weight, blood pressure, and glucose levels, the patient's genetics, and the patient's biographical parameters, such as age and location of residence.

It will be appreciated that the knowledge base 68 is expect to contain a large number of patient records. Accordingly, in one implementation, for each protein, the knowledge base 68 can simply be queried to return all or a predetermined number of records having all or a threshold number of biometric parameters relevant to establishing a baseline for that protein within a defined range around the patient's values for the biometric parameters. The time series for the protein can be averaged across all retrieved records to provide the baseline.

Once the baseline for biometric parameters has been calculated, each of the calculated baselines and a measured plurality of series of biometric parameters can be provided to a series of predictive models 73. The predictive models 73 can include any of appropriate supervised learning algorithms, such as regression models, artificial neural networks, support vector machines, and statistical classifiers, that predict a likelihood of one of a plurality of disorders according to deviations between the measured biometric parameters and the baseline. In one implementation, the predictive models 73 can include an analogical reasoning algorithm that compares the patient's measured biometric parameters, genetic markers, and clinical observation by a physician to sets of biometric parameters, genetic data, and observations from other patients for whom the presence or absence of a condition is known to determine a likelihood that the patient may experience the condition. The conditions evaluated by the predictive models 73 can be drawn from one or more disorder ontologies 74. A disorder ontology can be compiled from existing resources such as the International classification of Diseases (ICD), the Diagnostic and Statistical Manual of Mental Disorders (DSM), the Medical Dictionary for Regulator Activities (MedDRA), BioOntology, and the Open Biological and Biomedical Ontologies.

It will be appreciated that the system is not limited to a rigid disorder ontology. Many pathological states are defined by symptoms, leading to imprecise classifications. For example, it is likely chronic fatigue syndrome is an umbrella class for a host of different, possibly unrelated pathologies. Other disorders, such as autism and schizophrenia, exist along a spectrum of symptom intensities, which may also group states with different underlying causes. To this end, the system can provide a complementary way to define pathologies by the underlying biological data, rather than these imprecise symptom presentations. Specifically, unique combinations of biological data (e.g., genomic, proteomic, metabolomic) will be statistically processed and associated with outcomes and symptoms to provide more precise pathological classifications. By linking the biological state directly with the pathological classification, treatments can be assigned that directly address the underlying biological cause of symptoms.

The backwards analytics performed by the system can include one or more data mining algorithms 76 that analyze data stored in the knowledge base 68 for connections between previously unconnected predictors. The connections determined from the data mining algorithms 76 can be utilized to define new causality cases for use in the forward analytics performed by the system. This process can be fully automated, with new causality cases integrated into the predictive models 73 automatically, or in a semi-supervised fashion, in which each newly discovered causality case is reviewed by a subject matter expert before being incorporated into the predictive models. The data mining algorithms 76 can include, for example, anomaly detection algorithms, association rule learning, clustering algorithms, and sequential pattern mining.

In one implementation, new causality cases are generated as treatments, protein expression changes, and outcomes and then iteratively input into the knowledge base as adjustments of any of correlations, scoring, recommendations, and weighing of causalities. This information allows researchers to evaluate hypotheses and suggests subsequent research, such as identifying new biomarkers. As the system ingests and process new data, interesting relationships will emerge as analytics and data mining algorithms are automatically run. Researchers will be able to log in and bring up an updated list of trends and statistically significant relationships that have emerged. These lists serve as an opportunity for researcher to explore the meaning behind relationships and develop hypotheses for future research projects, thereby accelerating research productivity.

The system 50 also includes an analytics component 77 configured to retrieve data from the knowledge base 68 to confirm causality cases identified by the data mining component 76 and researchers. To this end, the analytics component 77 can include integration with the Basic Local Alignment Search Tool to find commonalities between a given genetic sequence and library sequences as well as various custom analytics algorithms that automatically discover correlations between baseline protein assays and diagnosed diseases later in life, automatically discover correlations between baseline protein assays and genetic sequences, and discover new genetic markers by correlating genome with diseases or allergic reactions. Further, the analytics component 77 can include an algorithm for tracking protein level changes associated with clinical treatment outcomes to explore the biological relationship to the proteins and disease, relate to genetic mutations, and develop more effective drugs using knowledge of the causal biological interactions. Finally, the analytics component 77 can include statistical analysis and analytic tools to assist researchers in confirming hypotheses generated by the data mining component 76 and the other analytic tools. In one implementation, the analytic tools can include advanced signal processing algorithms to extract correlations from noisy data and neural spike metrics.

Medications are often prescribed despite known side effects. The inventors have determined that the knowledge of who would be most likely to present with side effects is both within the capability of a learning healthcare information processing system 50 in accordance with the present invention and of considerable value, especially when alternative medications exist. Similarly, it would be to predict who may respond well and/or without side effects. To this end, the knowledge base 68 will be designed to collect outcome data fed back from the system 50. Positive and non-adverse outcomes may be unique for specific genetic mutations or baseline protein levels, and can therefore serve as additional information for supporting practitioner treatment recommendations and suggest areas of research and discovery. Outcomes will therefore be linked to specific genetic mutations and protein levels for individual patients to allow for prediction of patient response from proteomics and genomics.

It will be appreciated that the system may iteratively test hundreds to thousands of variables for significant correlations. While inclusion of more variables increases the probability of discovering insightful, actionable relationships, it also increases the probability of false positives. The standard approach to correct for this problem of "multiple comparisons" is to multiply significance test values by some corrective factor. For instance, in Bonferroni correction, the p value is multiplied by the number of independent tests performed. Unfortunately, this results in increasing the probability of false negatives. Therefore, the more independent significance tests run, the more interesting relationships will be buried into the background noise of non-significance.

In accordance with an aspect of the present invention, a rules engine 78 includes a mix of expert and machine-generated rules and weights are continuously deployed and tuned that learn which types of variables present the best probability for insightful or actionable results prior to analysis. The automated rules engine 78 is expected to supplement the efforts of expert researchers in determining what tests to run prior to a single research experiment. Reducing the overall number of tests will also optimize processing performance. Ultimately, the rules engine 78 mediates between statistical design and machine intelligence in developing healthcare-based statistical rules.

The results of the various analytics and modeling processes 70 can be provided to the knowledge base 68 to be added to the patient's record as well as any relevant medical databases 52. These records will generally be supplemented with a treatment record and a patient outcome once these factors are known. The results are also provided to respective visualization components 82-84. In one implementation, a researcher visualization component 82 presents the knowledge discovered by analytic search engines 77 applied to the genetic and proteomic data collected in this system in a visual fashion that is readily comprehendible. The researcher visualization component 82 can provide a user interface for analytic search algorithms to discover correlations between protein assays, genetic sequences, and diagnoses. The researcher visualization component 82 can also include various display and graphical manipulation tools to view protein level changes associated with clinical treatment outcomes so that the researcher can explore the biological relationship to the proteins and disease, relate the outcomes and proteins to genetic mutations, and develop more effective drugs using knowledge of the causal biological interactions. The researcher visualization component 82 can also provide a periodic report of emergent statistical associations between variables across databases as outcome data is fed back into the system, as well as simply access to relevant data and findings from valuable scientific databases.

A clinician decision support component 83 allows a clinician to access results of forward analytic processes for a given patient and relevant support information. For example, the clinician decision support component 83 can display to the clinician a list of diseases consistent with the patient's clinical observations, a latest protein assay, geographic location, and relevant environmental factors in likelihood order. The clinician can also instruct the clinician decision support component 83 to display a comparison of the current protein assay with the measured or imputed baseline assay, and/or a comparison the patient's history of protein assays with the normal time series of expected protein assays. The clinician decision support component 83 can also display values significant in the calculated baseline assay, such as markers from the patient's genome and exogeneous variables such as gender, weight, and age. The decision support component 83 can also notify a clinician when a patient has not been in contact with the office for a predetermined period of time or has failed to provide a scheduled biochemical assay. In one implementation, this notification can be complied over a period of time and provided in list form to avoid overwhelming the clinician.

A patient dashboard 84 can present the results of forward analytic processes and supporting data to a patient. To this end, the patient can be presented with any findings of elevated risk, the genomic, biochemical, and clinical parameters supporting the findings, and links to information related to the disorder or outcome associated with the elevated risk, potential treatments, and the parameters supporting the findings. For example, a patient could be provided with a link to information about the side effects associated with a prescribed medication. Any recommendations on health screening results and potential courses of action provided to the patient can include certainty-weighting and risk-based weighting to facilitate informed decisions by the patient. The dashboard 84 can also provide an interface for the patient to ask questions, via an encrypted e-mail service, such as S/MIME, to a clinician to clarify information received during an earlier visit. The dashboard 84 can also provide reminders to the patient for scheduled biochemical assays, appointments with clinicians, or to take or refill medicines. In one implementation, the patient can record observations of symptoms through the dashboard 84 as well review, correct, and supplement data in the patient's electronic medical record.

It will be appreciated that, after a medical outcome is known for a given patient, the knowledge base 68 can be updated to reflect the new result. To this end, a set of measured clinical outcomes 86 can be provided to the knowledge base 68 to augment the existing patient data. The measured clinical outcome can reflect, for example, whether the patient has a condition of interest after a set period of time after the prediction. Along with new medical research and new patient records entering the system, these patient outcomes 86 can provide the knowledge base 68 with the basis for new causality cases to be discovered by the analytics and modeling component 70.

In one example use case, a lab draws a patient's blood and provides the genomic 54 and proteomic 53 assays. In one implementation, the proteomic assay 54 can be performed using a low-cost, easily repeatable assay that can simultaneously determine levels for thousands of proteins from a small blood sample with a relatively low overhead for each testing site, allowing the test to be widely accessible. Since the test is designed to be low-cost and accessible, longitudinal data for a large population of individuals could be efficiently compiled. Once the data are normalized and processed, it can be determined if the patient's protein levels, taken in view of clinical observations of the patient, and genetic markers, indicate an enhanced likelihood of a given condition through the predictive models 73. In this example use case, it is determined that the patient has a genetic marker associated with a high risk of a particular type of cancer and elevated proteins associated with that type of cancer. The knowledge base 68 can include information indicating that a survival rate for this type of cancer is significantly higher when diagnosed within three months.

Once the enhanced risk of cancer is identified, a report is generated and the patient is notified. The patient can log into the patient dashboard 84 to view the report, which can include the diagnosis and links to information about the disorder, the proteomic and genetic data used to identify the elevated risk, and potential treatments. The report can also include a recommendation that the patient should schedule a visit with an oncologist. Similarly, a clinician associated with the patient, such as a family doctor and/or an oncologist treating the patient, can receive an alert through the clinician decision support component 83. The alert can be linked to a summary report, including an overall risk score associated with the diagnosis, the specific genetic markers and proteins relied upon for the diagnosis, with links to pertinent research, and visualization tools for viewing this data. The clinician's treatment decisions and the clinical outcome can be fed back into the knowledge base 68, along with information from follow-up visits, and comments from the patient and the clinician. These findings can then be made available to researchers, through the various tools available through the researcher visualization component 82, for further analysis.

In a second example use case, a researcher might view a summary report showing recently emergent data trends and find a high prevalence of non-adverse Pramipexole response for patients with elevated proteins associated with food allergies. The researcher could then search text within available journal articles via a text miner in the researcher visualization component 82 as well as data within the knowledge base and affiliated data sources for known relationships between a genetic mutation shared by patients who respond well to Pramipexole and the elevated protein. Assuming no known relationship is found, the researcher could develop and conduct tests to search for unidentified proteins that may also be elevated, with the hypothesis that any identified proteins might be elevated in some patients with fibromyalgia and cause increased sensitivity to allergies in patients with the genetic mutation.

The researcher can provide the results of the research and the determined hypothesis to the knowledge base and request that the proteomics lab develop an aptamer for the identified protein. Once the apatmer is generated, results from multiple patients undergoing their scheduled proteomic assays can be aggregated to confirm or refute the researcher's hypothesis. It will be appreciated that other information from the knowledge base 68 can be mined or queried to provide evidence supporting or refuting the hypothesis. Assuming that it is confirmed, further research can be performed, for example, via queries of the knowledge base 68 through the researcher visualization component 82, to find a drug that can be employed to reduce levels of this protein. This finding can then be fed back to the knowledge base 68 as a known relationship between the drug and fibromyalgia.

After all this has happened, a patient diagnosed with fibromyalgia might be determined by a clinician to be responding poorly to common medications. The clinician may wish to prescribe a dopamine agonist, but is concerned about efficacy and side effects. The clinician may instruct the patient to have blood drawn for a genomic or proteomic assay or utilize existing genomic and proteomic data from the scheduled assays for the patient. From this information, it might be determined that the patient shares the generic mutation associated with patients who respond to the dopamine agonist Pramipexole, but lacks a marker associated with patients who respond well to the dopamine agonist Ropinirole. The protein associated with increased sensitivity to allergies may also be found to be elevated in the patient. Information in the knowledge base can be automatically retrieved and provided to the clinician and the patient indicating that the protein expression level has been reduced in sixty percent of cases in which gluten has been removed from the diet.

All of this information can be provided to the clinician at the clinician decision support component 83 with a plurality of treatment options, each having an associated score representing the likelihood, generated from the predictive models 73, that the treatment will lead to a favorable clinical outcome. Two high-score treatments might include placing the patient on a gluten-free diet and prescribing Pramipexole. Accordingly, the clinician might select either option or combine the options, with the dosage of Pramipexole reduced to account for any beneficial effects of the gluten-free diet. To the extent that Pramipexole is prescribed, levels of proteins associated with the side effects can be tracked, for example, with the frequency of the patient's proteomic assays increased until the effects of the drug are clear.

The patient can also be provided with a summary report with the diagnosis, the treatment decision made by the clinician, and an appointment schedule. This report can include links to information related to diagnosis and treatment, such as online resources that describe fibromyalgia, side effects and interactions associated with the drug, and advice for pursuing a gluten-free diet. Information can also be provided for genetic markers and protein levels used in the diagnosis. The patient can use the patient dashboard 84 to record symptom levels, such as pain and fatigue, over time. Additionally, the level for the relevant proteins can be tracked over time to maintain the patient's awareness of their progress and possibly encourage compliance. The patient's reported symptoms and the clinician's observations can be fed back into the knowledge base 68 for use in evaluating the efficacy of the selected treatment and the prevalence of any side effects.

The illustrated system 50 provides a number of advantages. For example, the system enables economy of scale by testing numerous causality cases from a single blood sample. The system is capable of quantifying, aggregating, and disclosing measurement and recommendation certainty, including biosensor variability and any other potential source of error to ensure that the confidence associated with recommendations is meaningful to the patient and clinician, and the system can improve recommendation accuracy over time. As a result, the system can have sufficiently high reliability, capacity, and availability to support mission-critical use and scale with expected data increases over time, both in the available causality cases and the inclusion of new target populations.

Figure 3:
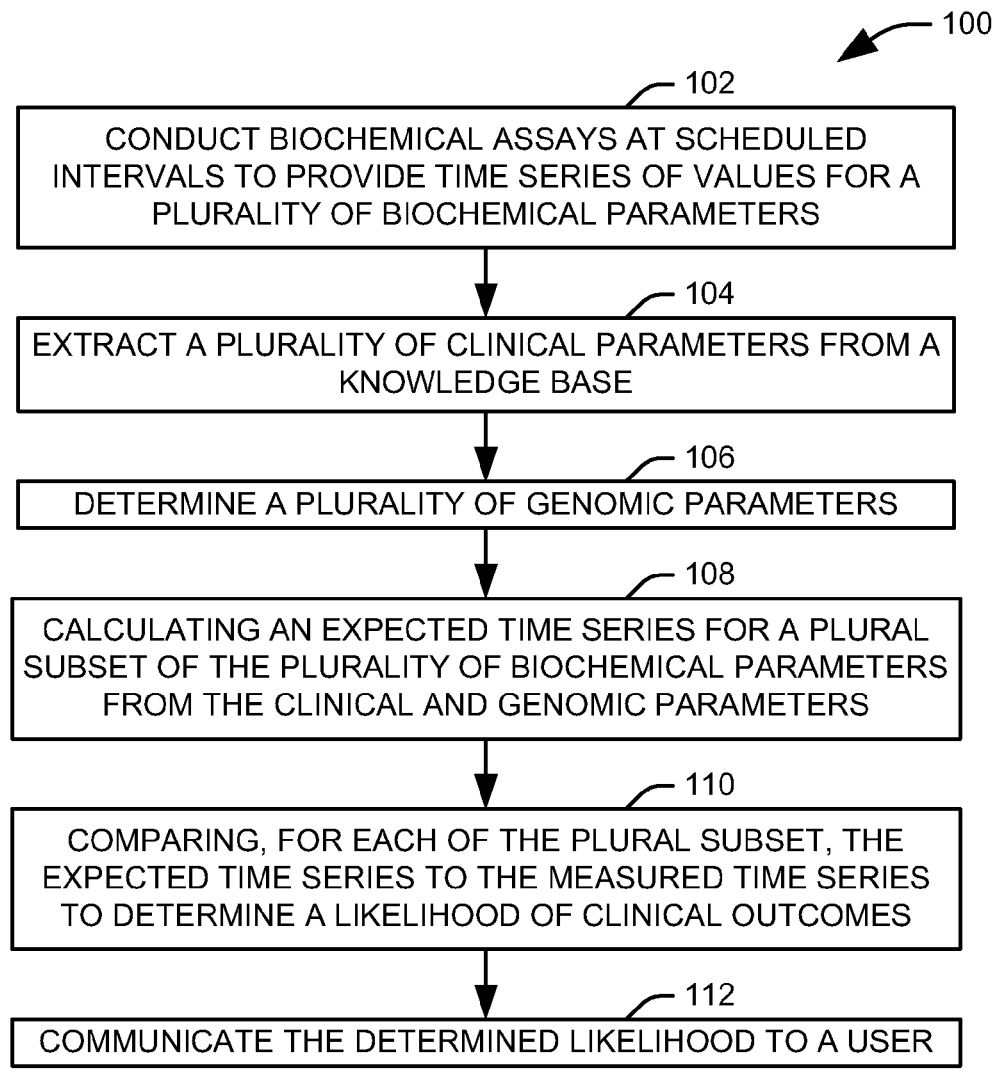
FIG. 3 illustrates a method for providing personalized healthcare support in accordance with an aspect of the present invention.
Figure 4:
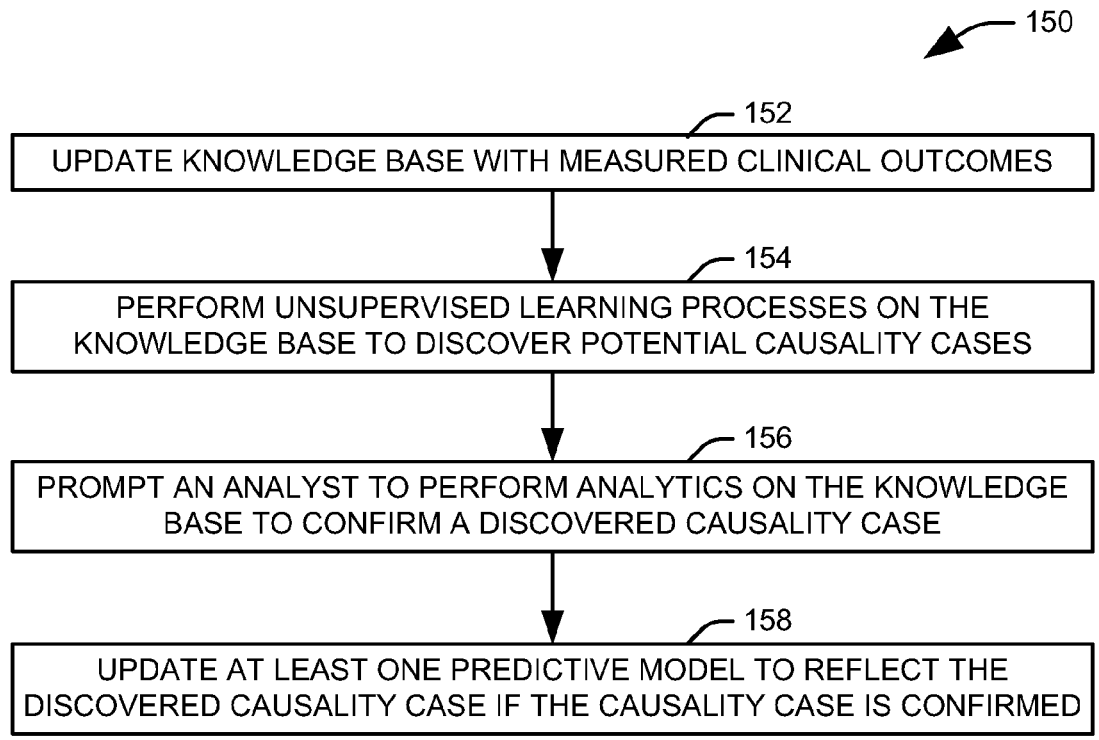
FIG. 4 illustrates a method for discovering and applying new causality cases in a learning healthcare system in accordance with an aspect of the present invention and FIG. 5 is a schematic block diagram illustrating an exemplary system of hardware components capable of implementing examples of the systems and methods disclosed in FIGS. 1-4.

In view of the foregoing structural and functional features described above in FIGS. 1 and 2, an example method will be better appreciated with reference to FIGS. 3 and 4. While, for purposes of simplicity of explanation, the method of FIGS. 3 and 4 are shown and described as executing serially, it is to be understood and appreciated that the present invention is not limited by the illustrated order, as some actions could in other examples occur in different orders and/or concurrently from that shown and described herein.

FIG. 3 illustrates a method 100 for providing personalized healthcare support in accordance with an aspect of the present invention. At 102, biochemical assays are conducted, at scheduled intervals, on a blood sample taken from an individual to provide a time series of values for each of a plurality of biochemical parameters. In one implementation, the biochemical assay is a baseline protein assay measuring a large number of protein levels from a single drop of blood, such that the assay can be low-cost and easily performed outside of a clinical environment. Accordingly, patient access to the biochemical assay can be made convenient to encourage compliance in generating a complete time series of values.

At 104, a plurality of clinical parameters, associated with the individual, from a knowledge base are extracted. The parameters can be categorical, such as diagnosed disorders or clinical observations of symptoms, as well as interval or ratio data, such as age, temperature, weight, blood pressure, cholesterol levels, and other such data. In one implementation, a plurality of cohort parameters can be extracted from respective series of biochemical assays in the knowledge base from record representing individuals who are associated with the individual. For example, the cohort parameters can include averaged time series of a given biochemical parameters across one or more of a set of people who are related to the patient, a set of people who live or work near the patient, and a set of people who share a condition or genetic marker in common with the patient.

At 106, a plurality of genomic parameters are determined for the individual. In one implementation, this can be done from the same blood sample used to derive the biochemical parameters. It will be appreciated that each of the time series of values and the plurality of genomic parameters can be stored in the knowledge base such that the knowledge base contains biochemical assays, genomic parameters, and clinical parameters for a population of patients.

Chemical and biological analysis is typically used to determine characteristic features of a biological sample. The features could then be transformed into representative quantitative values and provided to an information processing system for calculation and statistical analysis including data mining, machine learning and other computational functions. Many methods are known to those skilled in the art of biochemistry for determining signature features derived from biomedical samples and for comparing the features against other samples or across reference data sets. For example, comparing multiple mass spectra from different biological samples and identifying common features across the samples can be used as a reference condition, whereas identifying distinguishing features could serve as potential biomarkers for detection of an anomalous condition. The features can be compared across individuals and/or temporally for a specific individual. As described herein, various types of biochemical parameters are known and are available for use in analytics. The invention produces a greatly improved biochemical signature feature by combining multiple biochemical assays of different types and including a temporal component to the signature.

At 108, an expected time series is calculated for each of a plural subset of the plurality of biochemical parameters from at least the clinical parameters and the genomic parameters. For example, the expected time series can be determined as a weighted combination of time series values from patients having various characteristics associated with the clinical and genomic parameters of the patient, with the weight selected on a similarity, determined for example as a multivariate distance metric, between the patient and various other patients in the knowledge base. Alternatively, the knowledge base can be queried for patients having values for relevant biomedical parameters within a predefined range of the patient's values. The expected time series can be an unweighted average (e.g., mean or median) of the retrieved records.

In one embodiment, the invention calculates an expected time series by first representing the biochemical assays as feature vectors, each having a plurality of coefficients that correspond to a set of biochemical parameters. It then generates sets of clusters comprising pathological feature vectors derived from a large population of patients having a certain condition. The feature vector members of each specific cluster have signature similarities measured by a Euclidean distance calculation between the feature vector and the cluster centroid. Similarly, a well known unsupervised clustering method such as the K-means clustering algorithm can be used. Yet another alternative is to use a Mahalanobis distance for measuring similarity (correlation) with the advantage of being generally scale invariant. Furthermore, the combination of data sets and feature vectors that are associated with the biochemical assays can be represented in multiple dimensions as multivariate vectors or matrices and the clustering and distance calculations can be performed by fusing and correlating the multivariate vectors or matrices across the biochemical assay feature vector sets. There are many more distance measures and feature vector types that are known to those skilled in the art of statistical analysis. The embodiment described herein is shown only by way of example and it is understood that various alternatives can be used without a loss of generality.

The temporal aspect is now introduced where the sequences of cluster centroids are tracked over time and characterized by a cluster transition path. The time series value of an individual patient's biochemical assays can be compared to the expected time series by computing the distances of the associated feature vectors to the nearest-neighbor clusters, as each new blood sample is taken (e.g. on an annual basis). As an enhancement to the calculation, unnecessary features that are abundant in large bioinformatics data sets, and that do not materially contribute to system outcome/value, can be removed, thereby improving the results. Many other methods are available for performing supervised machine learning and data mining that are well known to those skilled in the art of data analysis.

At 110, for each of the plural subset of biochemical parameters, the time series of values representing the individual is compared to the calculated expected time series to determine a likelihood of each of a plurality of conditions for the individual. For example, a significant deviation of the time series of values from the calculated expected time series can be determined and applied as an input to a predictive model associated with one of the plurality of conditions, with the predictive model being configured to determine the likelihood of the associated one of the plurality of conditions from at least one parameter derived from the significant deviation. In one implementation, predictive models can be generated and refined by unsupervised learning processes mediated by subject matter experts. For example, a data mining algorithm can be applied to the knowledge base to identify at least one causality case relating one of the clinical parameters, the genomic parameters, and the cohort parameters to a condition. Once the causality case has been reviewed and verified by subject matter experts, for example, via the application of one or more analytic tools to retrieve evidence from the knowledge base, a predictive model can be refined or generated according to the identified causality case.

At 112, the likelihood of at least one of the plurality of conditions is communicated to a user. In one implementation, the user is the individual and the communication can include any or all of a healthcare treatment course of action, based on the communicated likelihood of the at least one condition, an instruction to the individual when a next biochemical assay should be scheduled based on the communicated likelihood of the at least one condition, and a recommendation as to a type of healthcare practitioner from which the individual should seek treatment. In another implementation, the user is a clinician and the communication includes a recommended protocol of care to the clinician based on the communicated likelihood of the at least one condition.

In one implementation, the communication is provided through a user interface that is configured to display to the user, for a selected one of the plural subset of biochemical parameters, a graphical representation of each of the time series representing the individual for the selected biochemical parameter and the calculated expected time series for the selected biochemical parameter, such that the calculated expected time series can be easily compared to measured values from the scheduled biochemical assays. The user interface can allow a clinician to select a new value from a selected one of the parameters used to calculate the expected time series and alter the graphical representation of the expected time series to reflect the new value of the selected parameter. This can allow the clinician to determine the effects of possible treatments and lifestyle modifications on a patient's health. It will further be appreciated that these tools can be made available to researchers for assistance in searching for new causality cases.

FIG. 4 illustrates a method 150 for discovering and applying new causality cases in a learning healthcare system in accordance with an aspect of the present invention. At 152, a knowledge base associated with the learning healthcare system can be updated with measured clinical outcomes for patients in the knowledge base. For example, the measured outcomes can be entered directly into the system via a user interface or retrieved from a medical records database. At 154, unsupervised learning processes are performed on the knowledge base to discover potential causality cases. The unsupervised learning processes can include, for example, anomaly detection algorithms, association rule learning, clustering algorithms, and sequential pattern mining.

At 156, an analyst is prompted to perform one or more analytics on the knowledge base to confirm a potential causality case. For example, a researcher might be provided with a summary report showing recently emergent data trends, with the appropriate supporting data available for review as text or a graphical representation. The researcher could then search text within available journal articles via a text miner or formulate one or more queries of related data in the knowledge base to develop a hypothesis for any emergent trends found to be of interest. The researcher could then develop and conduct tests to confirm the hypothesis, with the results of the research and the determined hypothesis provided to the knowledge base. If the hypothesis representing the causality case is confirmed, one or more predictive models are updated at 158 to reflect the new finding.

Figure 5:
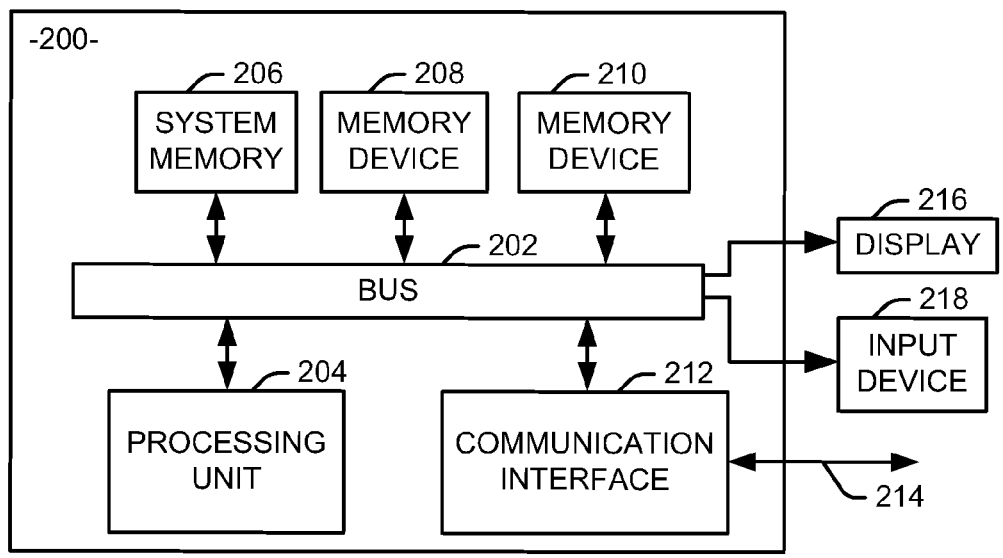

FIG. 5 is a schematic block diagram illustrating an exemplary system 200 of hardware components capable of implementing examples of the systems and methods disclosed in FIGS. 1-4, such as the learning health system illustrated in FIGS. 1 and 2. The system 200 can include various systems and subsystems. The system 200 can be a personal computer, a laptop computer, a mobile device, a tablet computer, a workstation, a computer system, an appliance, an application-specific integrated circuit (ASIC), a server, a server blade center, a server farm, etc.

The system 200 can includes a system bus 202, a processing unit 204, a system memory 206, memory devices 208 and 210, a communication interface 212 (e.g., a network interface), a communication link 214, a display 216 (e.g., a video screen), and an input device 218 (e.g., a keyboard and/or a mouse). The system bus 202 can be in communication with the processing unit 204 and the system memory 206. The additional memory devices 208 and 210, such as a hard disk drive, server, stand alone database, or other non-volatile memory, can also be in communication with the system bus 202. The system bus 202 interconnects the processing unit 204, the memory devices 206-210, the communication interface 212, the display 216, and the input device 218. In some examples, the system bus 202 also interconnects an additional port (not shown), such as a universal serial bus (USB) port.

The processing unit 204 can be a computing device and can include an application-specific integrated circuit (ASIC). The processing unit 204 executes a set of instructions to implement the operations of examples disclosed herein. The processing unit can include a processing core.

The additional memory devices 206, 208 and 210 can store data, programs, instructions, database queries in text or compiled form, and any other information that can be needed to operate a computer. The memories 206, 208 and 210 can be implemented as computer-readable media (integrated or removable) such as a memory card, disk drive, compact disk (CD), or server accessible over a network. In certain examples, the memories 206, 208 and 210 can comprise text, images, video, and/or audio, portions of which can be available in formats comprehensible to human beings.

Additionally or alternatively, the system 200 can access an external data source or query source through the communication interface 212, which can communicate with the system bus 202 and the communication link 214.

In operation, the system 200 can be used to implement one or more parts of a learning health system in accordance with the present invention. Computer executable logic for implementing the composite applications testing system resides on one or more of the system memory 206, and the memory devices 208, 210 in accordance with certain examples. The processing unit 204 executes one or more computer executable instructions originating from the system memory 206 and the memory devices 208 and 210. The term "computer readable medium" as used herein refers to a medium that participates in providing instructions to the processing unit 204 for execution.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications, and variations that fall within the scope of the appended claims.

What is claimed is:

1. A method for providing personalized health support comprising:
    conducting biochemical assays at scheduled intervals on blood samples taken from an individual to provide, for each of a plurality of biochemical parameters, a time series of values representing the individual;
    extracting a plurality of clinical parameters associated with the individual from a knowledge base;
    determining a plurality of genomic parameters for the individual;
  calculating an expected time series for each of a plural subset of the plurality of biochemical parameters from at least the clinical parameters and the genomic parameters;
    comparing, for each of the plural subset of biochemical parameters, the time series of values representing the individual to the calculated expected time series to determine a likelihood of each of a plurality of conditions for the individual;
    wherein comparing the time series of values representing the individual to the calculated expected time series to determine the likelihood of each of the plurality of conditions for the individual comprises:
  determining a deviation of the time series of values from the calculated expected time series;
  applying the deviation as an input to a predictive model associated with one of the plurality of conditions, the predictive model being configured to determine the likelihood of the associated one of the plurality of conditions from at least one parameter derived from the deviation;

outputting the likelihood of at least one of the plurality of conditions whereby a healthcare course of action can be made;

storing each of the time series of values, the plurality of genomic parameters, and measured clinical outcomes in the knowledge base such that the knowledge base contains biochemical assays, genomic parameters, clinical parameters, and measured clinical outcomes for a population of patients;

applying a data mining algorithm to the knowledge base to identify at least one causality case relating one of the clinical parameters, the genomic parameters, and the cohort parameters to a condition; and refining a predictive model according to the identified causality case.

2. The method of claim 1, wherein outputting the likelihood of at least one of the plurality of conditions comprises communicating the likelihood of at least one of the plurality of conditions to a user.

3. The method of claim 2, wherein the user is the individual, and communicating the likelihood of the at least one condition to a user comprises providing the individual with a healthcare treatment course of action, based on the communicated likelihood of the at least one condition.

4. The method of claim 3, wherein providing the individual with the healthcare treatment course of action comprises instructing the individual when a next biochemical assay should be scheduled based on the communicated likelihood of the at least one condition.

5. The method of claim 3, wherein providing the user with the healthcare treatment course of action comprises instructing the user to seek treatment from a specific type of healthcare practitioner.

6. The method of claim 2, wherein the user is a clinician, and communicating the likelihood of the at least one condition to a user comprises providing a protocol of care to the clinician based on the communicated likelihood of the at least one condition.

7. The method of claim 1, wherein outputting the likelihood of at least one of the plurality of conditions comprises providing the likelihood of at least one of the plurality of conditions to at least one of a knowledge base, a database, or a display, the outputted likelihood being available to at least one unsupervised learning process for updating a predictive model.

8. The method of claim 1, further comprising extracting a plurality of cohort parameters from respective series of biochemical assays representing individuals who are associated with the individual, and wherein the expected time series for each of the plural subset of the plurality of biochemical parameters is calculated from at least the clinical parameters, the genomic parameters, and the cohort parameters.

9. The method of claim 1, further comprises displaying to the user, for a selected one of the plural subset of biochemical parameters, a graphical representation of each of the time series representing the individual for the selected biochemical parameter and the calculated expected time series for the selected biochemical parameter, such that the calculated expected time series can be compared to measured values from the scheduled biochemical assays.

10. The method of claim 1, wherein the user is a clinician, and further comprising allowing the clinician to select a new value from a selected one of the clinical parameters and the genomic parameters used to calculate the expected time series and altering the graphical representation of the expected time series to reflect the new value of the selected one of the clinical parameters, the genomic parameters, and the cohort parameters.

11. A personalized healthcare system, implemented as machine executable instructions stored on a set of at least one non-transitory computer readable medium, each operatively connected to an associated processor, the system comprising:

a knowledge base comprising a record for each of a population of patients, a given record comprising a time series of values of a plurality of biochemical parameters taken from biochemical assays performed at scheduled intervals, a plurality of genetic markers, and a plurality of clinical parameters associated with the patient, the population of patients including, for each of a plurality of conditions of interest, a set of patients having the condition and a set of patients not having the condition;

a baseline calculation component configured to calculate, for a given patient, an expected time series for each of a plural subset of the biochemical parameters from at least the clinical parameters and the genomic parameters associated with the patient;

an analytics and modeling component configured to determine a deviation of the time series of values from the calculated expected time series and apply the deviation as an input to a predictive model associated with one of the plurality of conditions, the predictive model being derived from data associated with each of the set of patients having the condition and the set of patients not having the condition and configured to determine the likelihood of that the patient has the condition from at least one parameter derived from the deviation; and a user interface configured to provide the determined likelihood that the patient has the condition to a user;

wherein a measured clinical outcome, reflecting at least whether the patient has the condition after a predetermined period of time, is provided to the knowledge base, the analytics and modeling component comprising a data mining component configured to perform a plurality of unsupervised learning algorithms on the knowledge base to determine at least one causality case relating one of the clinical parameters and the genomic parameters to the condition;

the analytics and modeling component further comprising an analytics component available to the user through the user interface and configured to retrieve data from the knowledge base and an associated database to provide evidence supporting a causality case of the at least one causality case determined by the data mining component.

12. The system of claim 11, the analytics and modeling component further comprising a rules engine that evaluates causality cases determined by the data mining component, according to an associated set of rules, to determine which variables, associated with the causality cases, present a highest likelihood of providing actionable results if evaluated with the analytics component.

13. The system of claim 11, wherein the plurality of clinical parameters associated with the patient include at least one of an age, a weight, a blood pressure, and a temperature of the patient.

14. The system of claim 11, wherein the user interface comprises a patient dashboard configured to communicate each of the likelihood of the condition, a healthcare treatment course of action, and a scheduled next biochemical assay.

15. The system of claim 11, further comprising a research interface incorporating an information extraction component to reduce an unstructured source of research into a template compatible with the knowledge base.

16. The system of claim 11, wherein the user interface comprises a clinician decision support component configured to communicate a recommended protocol of care to a clinician based on the determined likelihood that a patient has a condition.

17. A method for providing personalized healthcare for a patient comprising:
- conducting biochemical assays at scheduled intervals on blood samples taken from an patient to provide, for each of a plurality of biochemical parameters, a time series of values representing the patient;
- extracting a plurality of clinical parameters associated with the patient from a knowledge base;
- determining a plurality of genomic parameters for the patient;
- extracting a plurality of cohort parameters from respective series of biochemical assays representing individuals who are associated with the patient;
- calculating an expected time series for each of a plural subset of the plurality of biochemical parameters from at least the clinical parameters, the cohort parameters, and the genomic parameters;
- determining a deviation of the time series of values from the calculated expected time series;
- applying the deviation as an input to a predictive model associated with a condition, the predictive model being configured to determine the likelihood of the condition from at least one parameter derived from the deviation;
- providing the user with a healthcare treatment course of action, based on the likelihood of the conditions;
- storing each of the time series of values, the plurality of genomic parameters, and measured clinical outcomes in the knowledge base such that the knowledge base contains biochemical assays, genomic parameters, clinical parameters, and measured clinical outcomes for a population of patients;
- applying a data mining algorithm to the knowledge base to identify at least one causality case relating one of the clinical parameters, the genomic parameters, and the cohort parameters to a condition; and
- refining a predictive model according to the identified causality case.

* * * * *